United States Patent [19]

Adams et al.

[11] 3,969,402

[45] July 13, 1976

[54] PHENYLALKANOIC ACIDS

[75] Inventors: Stewart S. Adams; Bernard J. Armitage; John S. Nicholson, all of Nottingham, England

[73] Assignee: The Boots Company Limited, Nottingham, England

[22] Filed: June 6, 1973

[21] Appl. No.: 367,614

[30] Foreign Application Priority Data

June 15, 1972 United Kingdom............... 28104/72

[52] U.S. Cl.......................... 260/520 R; 260/307 F; 260/453 R; 260/465 G; 260/471 A; 260/473 S; 260/519; 260/559 D; 260/575; 260/592; 260/600 R; 424/272; 424/308; 424/317; 424/324; 424/346
[51] Int. Cl.$^2$......................................... C07C 65/14
[58] Field of Search............. 260/473 R, 473 S, 520

[56] References Cited
UNITED STATES PATENTS

| 3,624,142 | 11/1971 | Shen et al. | 260/473 R |
| 3,671,580 | 6/1972 | Shen et al. | 260/473 S |

FOREIGN PATENTS OR APPLICATIONS

| 1,091,403 | 11/1967 | United Kingdom | 260/473 |

*Primary Examiner*—Paul J. Killos
*Attorney, Agent, or Firm*—Lawrence Rosen; E. Janet Berry

[57] ABSTRACT

New compounds are described that are 2-(hydroxy substituted-4-biphenylyl)propionic acids. Processes of making and using them and pharmaceutical compositions containing them are also described. The compounds have, inter alia, antiinflammatory activity.

1 Claim, No Drawings

PHENYLALKANOIC ACIDS

This invention relates to novel substituted propionic acids and derivatives thereof which have been found to possess valuable biological properties.

According to one feature of the invention there are provided novel compounds of the general formula I

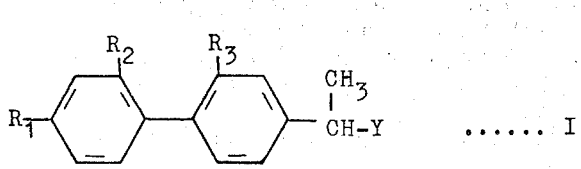

wherein $R_1$, $R_2$ and $R_3$ are individually selected from hydrogen, halogen and hydroxy, provided that at least one of $R_1$, $R_2$ and $R_3$ is hydroxy, and Y is COOH, $CONH_2$, $CH_2OH$, CONHOH or

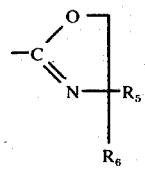

wherein $R_5$ and $R_6$ are the same or different alkyl or hydroxyalkyl, together with pharmaceutically acceptable esters (i.e. compounds wherein Y is $COOR_4$ in which $R_4$ is an esterifying radical) and pharmaceutically acceptable salts of those compounds wherein Y is COOH or CONHOH. The salts may be formed with inorganic or organic bases. The term "halogen" designates chlorine, bromine or fluorine.

The compounds of general formula I possess anti-inflammatory activity and are useful for the treatment of inflammatory conditions. They also possess analgesic and antipyretic properties and are useful for the treatment of conditions of pain and pyretic conditions. Their activity has been determined in experimental animals using pharmacological tests which are known to be capable of characterising compounds possessing the therapeutic properties of aspirin, namely anti-inflammatory, analgesic and antipyretic activity.

The therapeutic activity of the compounds is assessed in various ways. For example the anti-inflammatory activity is determined in the test described by Adams and Cobb, Nature 1958, 181, 733. The activity of the test compounds is compared with that of aspirin against ultra-violet light induced erythema on the depilated skin of guinea pigs.

Another way of determining anti-inflammatory activity is by the rat adjuvant arthritis test in which an arthritis is produced by injecting intradermally into the tail 0.1 ml. of a suspension of killed human tubercle bacilli (6 mg./ml.) in liquid paraffin BP. A polyarthritis develops over the next 3 weeks in untreated controls. The compounds under test (vehicle only for control animals) are given daily by mouth from the day the adjuvant is injected for 21 days. On day 21 the degree of arthritis is assessed on each hind foot. The degree of inhibition produced by a compound is estimated by comparison of the total arthritic scores with those found in the controls.

The analgesic activity of the compounds is determined in the rat using a modification of the technique described by Randall and Selitto, Arch. int. Pharmacodyn, 1957, 111, 409. In this technique the analgesic effect of the drugs is compared with aspirin by determining the increase in pain threshold when pressure is applied to the inflamed foot.

The anti-pyretic effect is determined in rats in which the body temperature has been raised by a subcutaneous injection of a yeast suspension. Comparison of the compounds under test is made with graded doses of aspirin.

Preferred compounds of the invention are those wherein Y is COOH. It is believed that when salts, esters, the amide or the alcohol derived from the acid are used in place of the acid said derivatives are metabolised by the animal body and are converted in the body into the corresponding acid.

It will be appreciated that, since the compounds of general formula I possess an asymmetric carbon atom, they are ordinarily present in the form of a racemic mixture. The resolution of such racemates may be carried out by any conventional method and the separated optically active stereoisomers form part of the present invention.

The compounds of the invention may be administered in the conventional manner of aspirin or usual manner for other anti-inflammatory, analgesic, and antipyretic agents, for example orally, topically, rectally or parenterally, preferably orally. The optimum dosage rate varies with the route of administration, but normally lies within the range 0.03 – 60 mg./kg./day, more usually between 0.70 – 30 mg./kg./day. The unit dose may vary from 1 mg. to 1000 mg. per subject; for oral administration the dosage rate is preferably 2 – 2000 mg. per subject per day, optionally in divided doses.

In use, the compounds of the invention are administered in conventional formulations and accordingly the invention also provides therapeutic compositions which comprise, as an active ingredient, a compound of the invention together with a pharmaceutically acceptable carrier. Pharmaceutically acceptable carriers suitable for the production of compositions for oral, topical, rectal or parenteral administration are well known in the art. The compositions of the invention suitably contain 0.1 – 90% by weight of a compound of the invention.

Compositions for oral administration are the preferred compositions of the invention, and these are the conventional pharmaceutical forms for such administration, such as for example tablets, capsules, lozenges, powders, effervescent granules, syrups and aqueous and oily suspensions. The excipients used in the preparation of these compositions are the excipients of the pharmacist's art. Thus in the preparation of tablets, typical excipients include disintegrating agents, for example maize starch and lubricating agents such as magnesium stearate; in the preparation of capsules, standard gelatin capsules may be used containing the active ingredient alone or admixed with a diluent. The liquid compositions may comprise as excipients water and sucrose to provide syrups, water, dispersing agents and suspending agents, for example sodium carboxymethylcellulose to provide aqueous suspensions, and a non-toxic oil, for example a vegetable oil such as arachis oil and a suspending agent to provide oily suspensions.

Compositions for rectal administration are the conventional pharmaceutical forms for such administration, such as for example suppositories with cocoa butter or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1 – 4 carbon atoms which may contain a small proportion of water.

Compositions for parenteral administration are the conventional pharmaceutical forms for such administration, for example sterile suspensions in aqueous or oily media or sterile solutions in propylene glycol.

In some formulations it may be beneficial to use the compounds of the invention in the form of particles of very small size, such as for example, as obtained by fluid energy milling, for example micronizing.

The invention further provides a method of treating inflammatory conditions, conditions of pain and pyretic conditions, individually or in any combination, in warm-blooded animals including man, which comprises administering a compound of the invention, preferably orally.

The products of the present invention may of course be employed in combination with other active anti-inflammatory agents, analgesics, and antipyretic agents, or with other drugs, as is already conventional in the art for other existing anti-inflammatory, analgesic and anti-pyretic materials such as aspirin.

The compounds of the invention have other valuable properties. For example, they possess fibrinolytic and thrombolytic activity and also inhibit platelet aggregation induced by various agents such as adrenaline.

The fibrinolytic activity is assessed by the euglobulin lysistime test described by Van Kaulla in Chemistry of Thrombolysis: Human Fibrinolytic Enzyme, 1963, p79, published by Charles C. Thomas, Springfield, Illinois.

The thrombolytic activity is assessed by the hanging clot test described by Van Kaula, J. Med. Chem. 1965, 8, 164.

The effect on platelet aggregation is assessed by the test of Born; Nature, 1962, 194, 927.

Drugs possessing such properties are useful in the treatment and/or prophylaxis of various thrombotic disorders. When being used in such treatment or prophylaxis they may be formulated and administered in a manner similar to that when being used as anti-inflammatory agents, as described previously.

Typical compounds of the invention include the following compounds.

2-(2-fluoro-4′-hydroxy-4-biphenylyl)propionic acid
2-(4′-fluoro-2-hydroxy-4-biphenylyl)propionic acid
2-(4′-chloro-2-hydroxy-4-biphenylyl)propionic acid
2-(2-chloro-4′-hydroxy-4-biphenylyl)propionic acid
2-(2-bromo-4′-hydroxy-4-biphenylyl)propionic acid
2-(2-hydroxy-4-biphenylyl)propionic acid
2-(2,4′-dihydroxy-4-biphenylyl)propionic acid
2-(4′-fluoro-2′-hydroxy-4-biphenylyl)propionic acid
2-(2′-fluoro-2-hydroxy-4-biphenylyl)propionic acid
2-(2,4′-dichloro-2′-hydroxy-4-biphenylyl)propionic acid
2-(4′-hydroxy-4-biphenylyl)propionic acid
2-(2′-chloro-4′-fluoro-2-hydroxy-4-biphenylyl)propionic acid
2-(2-chloro-4′-fluoro-2′-hydroxy-4-biphenylyl)propionic acid
2-(2-chloro-2′,4′-dihydroxy-4-biphenylyl)propionic acid
2-(2-fluoro-2′-hydroxy-4-biphenylyl)propionic acid
2-(2-chloro-2′-hydroxy-4-biphenylyl)propionic acid
2-(2′-hydroxy-4-biphenylyl)propionic acid
2-(2,2′-dihydroxy-4-biphenylyl)propionic acid
2-(2′,4′-difluoro-2-hydroxy-4-biphenylyl)propionic acid
2-(2,4′-difluoro-2′-hydroxy-4-biphenylyl)propionic acid
2-(4′-chloro-2-fluoro-2′-hydroxy-4-biphenylyl)propionic acid
2-(2,2′-difluoro-4′-hydroxy-4-biphenylyl)propionic acid
2-(2-fluoro-2′,4′-dihydroxy-4-biphenylyl)propionic acid
2-(2,2′,4′-trihydroxy-4-biphenylyl)propionic acid
sodium 2-(2-fluoro-4′-hydroxy-4-biphenylyl)propionate
methyl 2-(2-fluoro-4′-hydroxy-4-biphenylyl)propionate
sodium 2-(2-hydroxy-4-biphenylyl)propionate
methyl 2-(2-hydroxy-4-biphenylyl)propionate
ethyl 2-(2′,4′-difluoro-2-hydroxy-4-biphenylyl)propionate
2-[1-(2′,4′-difluoro-2-hydroxy-4-biphenylyl)ethyl]-4,4-dimethyl-2-oxazoline.
2-(2′,4′-difluoro-2-hydroxy-4-biphenylyl)propionamide
2-(2′,4′-difluoro-2-hydroxy-4-biphenylyl)propan-1-ol
2-(2-hydroxy-4-biphenylyl)propionhydroxamic acid The compounds of the invention may be prepared by removing any phenolic protecting group X from a compound of the general formula II

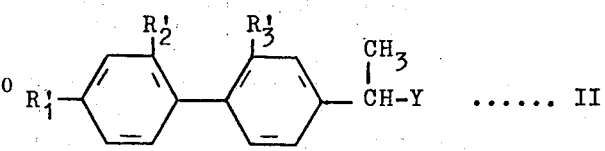

wherein Y is as hereinbefore defined and wherein $R_1'$, $R_2'$ and $R_3'$ are individually selected from hydrogen, halogen, hydroxy and OX, provided that at least one of $R_1'$, $R_2'$ and $R_3'$ is OX. It will be appreciated that two or three of $R_1'$, $R_2'$ and $R_3'$ may be OX.

Phenolic protecting groups X are well known in the art and include, for example, lower alkyl (preferably methyl), benzyl and tetrahydropyranyl. Thus, for example, a lower alkoxy (preferably methoxy) or benzyloxy group may be converted to hydroxy by dealkylation (preferably demethylation) or debenzylation, which may be effected, for example, by heating with HBr in a suitable solvent such as aqueous acetic acid. As another example, benzyloxy may be converted to hydroxy by hydrogenolysis. Such hydrogenolysis may be carried out in a conventional manner, for example by reaction with hydrogen at atmospheric pressure or above in the presence of a suitable catalyst, for example palladium on charcoal or platinum oxide. As a further example, a tetrahydropyranyloxy group may be converted to hydroxy in a conventional manner, for example by reaction with a suitable acid, for example a mineral acid, in a suitable aqueous solvent.

The intermediate compounds of general formula II may be prepared by methods analogous to those described in our British patent specification No. 1,091,403 and Belgian patent specifications Nos. 764257 and 764258.

Further typical methods for the preparation of the compounds of the invention are as follows. Processes for the preparation of the stated starting materials and exact reaction conditions for the typical methods described will be readily apparent to those skilled in the art and, further, typical methods for the preparation of starting materials are given in some of the examples. In the following description for the preparation of the acids and the various acid derivatives the symbol $R_0$ has been used to represent the radical

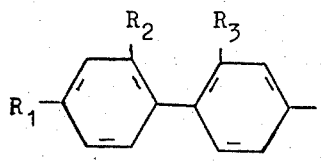

wherein $R_1$, $R_2$ and $R_3$ are as hereinbefore defined.

ACIDS

1. Hydrolysis of a compound of general formula III

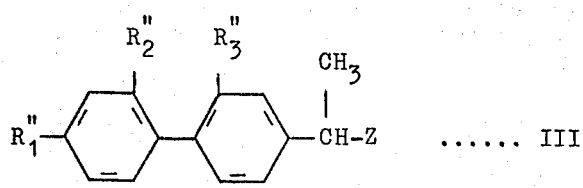

wherein Z is cyano, carbamoyl, N,N,-disubstituted thiocarbamoyl (preferably derived from morpholine), $COOR_4$ in which $R_4$ is an ester forming group, especially lower alkyl or

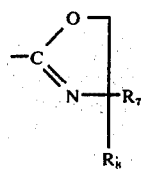

wherein $R_7$ and $R_8$ are the same or different and are alkyl or aryl or together with the carbon to which they are bonded form a carbocyclic ring; and $R_1''$, $R_2''$ and $R_3''$ are selected from hydrogen, halogen, hydroxy or —OG, in which G is a phenolic protecting group which is removed under the hydrolysis conditions, at least one of $R_1''$, $R_2''$ and $R_3''$ being hydroxy or —OG.

The hydrolysis may be carried out according to methods well known in the art, for example by the use of acid or alkali in water, in an organic liquid reaction medium, or in a mixture thereof; a treatment temperature of 15° – 150°C. is convenient. Preferably the hydrolysis is carried out by refluxing in the presence of an alkali metal hydroxide or of a mineral acid, and the organic liquid reaction medium is a lower alkanol.

When one of the R'' groups is —OG this may be, for example, lower alkyl (preferably methyl), benzyl or tetrahydropyranyloxy, which, if the hydrolysis is carried out using a mineral acid, will be converted to a hydroxy group during the course of the conversion to the acid.

The starting materials may be prepared by conventional means, usually from the corresponding substituted acetophenone,

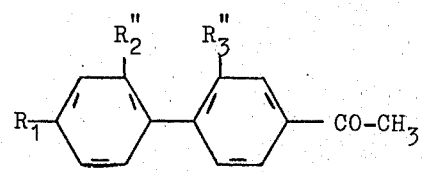

Methods also include those outlined below under the "Esters" and "Amides" headings.

Starting materials in which Z is

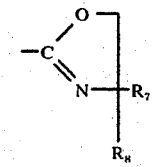

may be obtained, for example, by the methods described for related compounds in our German OLS 2241913.

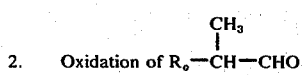

2. Oxidation of $R_0$—CH—CHO    IV

The oxidation may be carried out using any suitable oxidising agent such as per acids, hydrogen peroxide, silver oxide, or oxygen. A very convenient procedure involves oxidation in aqueous ethanol with alkali (for example an alkali metal hydroxide) and silver oxide.

The starting materials may be prepared by the methods described for related compounds in our British patent specification No. 1,160,725.

3. Reductive cleavage of a compound of general formula V

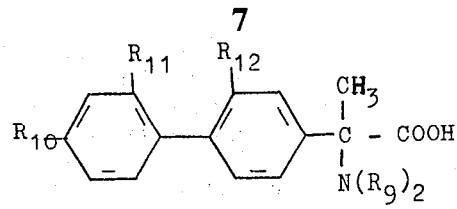 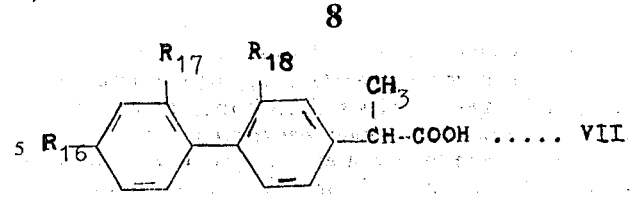

in which $R_9$ is alkyl, and $R_{10}$, $R_{11}$, and $R_{12}$ are selected from hydrogen, halogen, hydroxy or —OQ, in which Q is a phenolic protecting group which is removable under the reductive cleavage conditions, at least one of $R_{10}$, $R_{11}$ and $R_{12}$ being hydroxy or —OQ. This may be achieved by conventional methods such as by catalytic hydrogenation for example using a palladium charcoal catalyst, or by treatment with sodium in liquid ammonia.

When one of the R groups is —OQ this may be, for example, benzyloxy, which will be converted to a hydroxy group during the hydrogenation.

The starting materials may be prepared by the methods described for related compounds in our British patent specification No. 1,167,192.

4. Hydrogenation of a compound of general formula VI in which at least one of the symbols $R_{16}$, $R_{17}$ and $R_{18}$ is an amino group and the other symbols correspond to the desired values of $R_1$, $R_2$ or $R_3$, in known manner, so as to convert said amino group to halogen or hydroxy. Examples for known procedures for introducing halogen include the Sandmeyer reaction, wherein the amino compound is diazotised and reacted with a cuprous halide, and the Schiemann reaction wherein the amino compound is diazotised in the presence of a fluorinating agent to form a fluorodiazonium derivative which is then decomposed by heating to give the corresponding fluoro compound. Suitable fluorinating agents include hydrogen fluoride, fluoboric acid, fluosilicic acid and hexafluorophosphoric acid. The amino group may be converted to hydroxy e.g. by diazotization and decomposition of the diazonium salt with aqueous mineral acid.

6. Replacement of halogen by OH in a compound of the general formula VIII

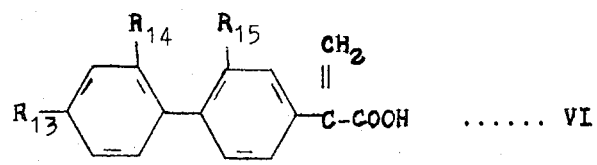 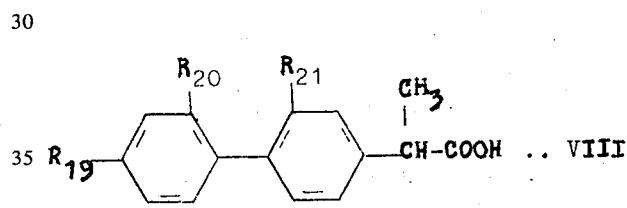

or an ester, amide or oxazoline thereof in which $R_{13}$, $R_{14}$ and $R_{15}$ are selected from hydrogen, halogen, hydroxy or —OT in which T is a phenolic protecting group which is removable under the hydrogenation conditions at least one of $R_{13}$, $R_{14}$ and $R_{15}$ being hydroxy or —OT.

Typical procedures include hydrogenation over a conventional catalyst such as, for example, palladium, palladium oxide or platinum in an inert solvent such as a lower alkanol, benzene, toluene, xylene, tetrahydrofuran, dioxan and acetic acid, at a temperature of about 0°C. up to the reflux temperature of the system.

When one of the R groups is —OT, this may be for example benzyloxy, which will be converted to a hydroxy group during the hydrogenation.

The starting materials may be prepared conventionally such as for example, in which Ar is the biphenylyl group wherein $R_{19}$, $R_{20}$ and $R_{21}$ are individually selected from hydrogen, halogen and hydroxy, at least one of $R_{19}$, $R_{20}$ and $R_{21}$ being halogen. This reaction may be effected, for example, by heating the compound of general formula VIII with potassium hydroxide in a suitable solvent, for example ethylene glycol.

7. Decarboxylation of a compound of formula IX

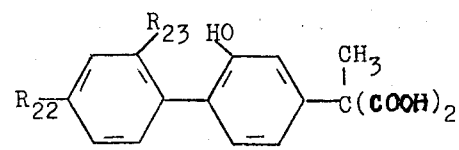

wherein $R_{22}$ and $R_{23}$ are hydrogen or halogen. The decarboxylation reaction may be effected by heating compound IX at a suitable temperature, for example 180° – 220°C. Compound IX may be prepared from 2-phenyl-o-quinol acetate (Wesseley et al., *Monatsh.* 1952, 83, 1260) as follows:

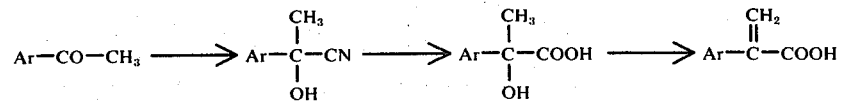

5. Reaction of a compound of general formula VII

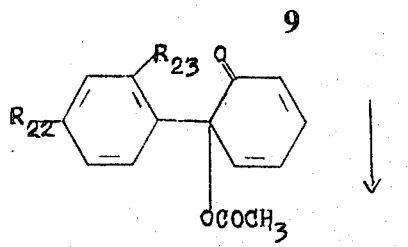 + 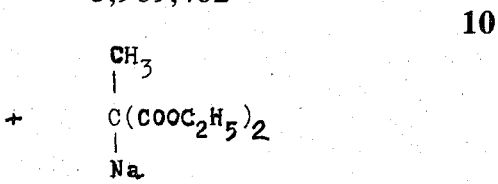

↓

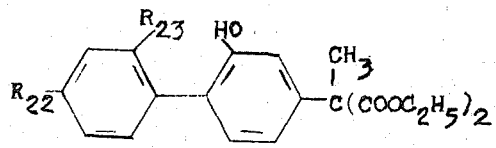 →  aqueous NaOH

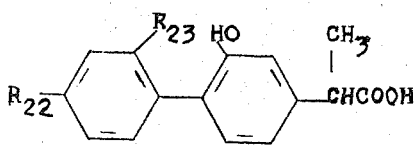

ESTERS

1. Esterification of the acids by conventional means, for example:

(a) $R_o\text{—CH(CH}_3\text{)—COOH} + R_4\text{OH} \longrightarrow R_o\text{—CH(CH}_3\text{)—COOR}_4$ or $R_o\text{—CH(CH}_3\text{)—COHal} + R_4\text{OH} \longrightarrow R_o\text{—CH(CH}_3\text{)—COOR}_4$ (b) $R_o\text{—CH(CH}_3\text{)—COOH} + CH_2N_2 \longrightarrow R_o\text{—CH(CH}_3\text{)—COOCH}_3$
(diazomethane)

2. Alcoholysis of $R_o\text{—CH(CH}_3\text{)—Z}_1$, wherein $Z_1$ is cyano, carbamoyl, N,N-disubstituted thiocarbamoyl (for example derived from morpholine) or

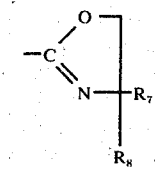

3. By means of methods (4) or (5) as described under "Acids" but starting with the desired ester in place of the acid.

The esterifying group $R_4$ may be a hydrocarbon radical containing up to 10 carbons, for example benzyl or lower alkyl, but any suitable esterifying group may be used. $R_4$ is preferably lower alkyl. The term "lower" designates a radical containing 1 – 7 carbon atoms, preferably 1 – 4 carbon atoms.

AMIDES

Preparation of the amides by conventional means, for example:

1. $R_o\text{—CHCOHal(CH}_3\text{)} + NH_3 \longrightarrow R_o\text{—CHCONH}_2(CH_3)$ 2. $R_o\text{—CHCN(CH}_3\text{)} \longrightarrow R_o\text{—CH(CH}_3\text{)—CONH}_2$ 3. By means of methods (4) or (5) as described under "Acids" but starting with the amide in place of the acid.

SALTS

1. Reaction of the acids with organic or inorganic bases.
2. Alkaline hydrolysis of

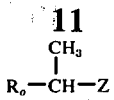

Typical inorganic salts that may be formed are the sodium and potassium salts. Typical organic salts that may be formed are amine salts, including hydroxy amine salts. For example salts with triethylamine or diethylaminoethanol or benzylamine may be formed.

ALCOHOLS

1. Reduction of the acids or, preferably, the esters (especially alkyl esters). The use of lithium aluminium hydride in a suitable solvent for example ether, followed by acidification, is one example. Alternatively hydrogenation in the presence of a copper/chromium oxide catalyst may be used. Esters may be reduced with sodium in a lower alkanol.

2. By means of method (5) as described under "Acids" but starting with a protected alcohol in place of the acid. The alcohol may be protected by a conventional readily removable group for example benzyl, which is finally removed after the earlier synthesis stages.

OXAZOLINES

1. Preparations from the acids by conventional means, for example:

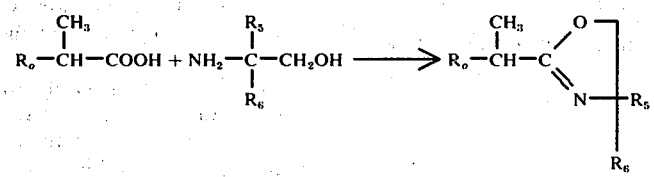

2. By means of methods (4) or (5) as described under "Acids" but starting with the desired oxazoline in place of the acid.

HYDROXAMIC ACID

Preparation by conventional means: e.g.

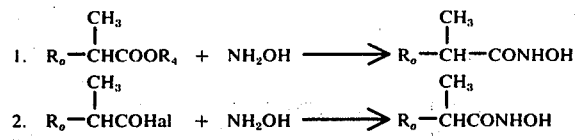

The invention is illustrated in the following examples in which "parts" and "percentages" are by weight unless otherwise stated. In the Examples the term "ether" denotes diethyl ether.

EXAMPLE 1 a. A stirred mixture of 4-iodoanisole (174.5 g.), 4'-bromo-3'-nitroacetophenone (162.5 g.) and copper powder (144 g.) was heated at 80°C. for 5 hours and the temperature was then gradually raised during 4 hours to 110°C. The stirred mixture was maintained at 110°C. for a further period of 3 days. The reaction mixture was cooled to room temperature and extracted with methylene dichloride. The extract was filtered and the filtrate evaporated under reduced pressure to remove methylene dichloride. The residue was distilled in vacuo to give the product, b.p. 200° – 210°C./0.6 mm., which solidified on cooling. This product was recrystallized from methanol to give 4-acetyl-4'-methoxy-2-nitrobiphenyl, m.p. 127° – 129°C. (novel intermediate A).

b. Intermediate A (65 g.) was added during 45 minutes to a stirred and warmed solution of 300 g. stannous chloride (300 g.) in a mixture of concentrated hydrochloric acid (440 ml.) and ethanol (600 ml.). The resulting solution was refluxed for 3 hours and then the ethanol was removed by evaporation in vacuo. The cooled residue was poured onto a solution of sodium hydroxide (650 g.) in a mixture of water and ice. A solid product separated out which was extracted into methylene dichloride. The extract was washed with water, dried over anhydrous sodium sulphate, and evaporated. The solid residue was recrystallized from ethanol to give 4-acetyl-2-amino-4'-methoxybiphenyl m.p. 157° – 161°C. (novel intermediate B).

c. To a stirred solution of intermediate B (8.8 g.) in a mixture of tetrahydrofuran (28 ml.), water (9.5 ml.) and hydrofluoroboric acid (38.5 ml. of 42% w/$_v$ acid) was slowly added a solution of sodium nitrite (2.7 g.) in water (4.5 ml.) whilst maintaining the temperature of the reaction mixture below 5°C. The mixture was then stirred for a further period of 20 minutes at 0° – 5°C. The resulting diazonium fluoroborate was collected by filtration, washed with hydrofluoroboric acid (20 ml. of 10% w/$_v$ acid) and then with methanol/ether (60 ml. of 10% methanol in ether), and finally dried in vacuo. This product was suspended in xylene (85 ml.) and the suspension heated to 70°C. at which point decomposition took place. When the reaction had subsided the mixture was refluxed for 45 minutes, after which the xylene was removed by distillation in vacuo. The residue was extracted with hot benzene. The resulting extract was cooled, washed with dilute aqueous sodium carbonate and then water, dried over anhydrous sodium carbonate, and evaporated. The residue was distilled in vacuo to give a product, b.p. 146° – 156°C./0.2 mm. which solidified on cooling. This product was recrystallized from ethanol to give 4-acetyl-2-fluoro-4'-methoxybiphenyl, m.p. 103° – 106°C. (novel intermediate C).

d. Intermediate C (3.93 g.) was added to a stirred solution of sodium (0.65 g.) in isopropanol (42 ml.). The resulting stirred slurry was cooled to 5°C. and ethyl chloroacetate (3.5 ml.) was added dropwise. The reaction mixture was stirred for 5 hours, allowing the temperature of the mixture to rise to room temperature, and then kept overnight. The mixture was evaporated under reduced pressure to remove isopropanol and the residue was refluxed with stirring for 45 minutes with a mixture of aqueous sodium hydroxide (18N; 1.8 ml.) and 10%v/$_v$ aqueous ethanol (10%v/$_v$; 25 ml.). Ethanol was removed from the mixture by distillation in vacuo and the residue was diluted to 200 ml. with water. To the resulting mixture was gradually added sodium metabisulphite (8.75 g.) with stirring and heated on the steam bath. After heating for a total period of 6 hours the resulting suspension was cooled, stirred with ether (20 ml.) and slowly treated aqueous with sodium hydroxide (18N; 3 ml.). The ethereal layer was separated, washed with dilute acetic acid and then with water, dried over anhydrous sodium carbonate and evaporated under reduced pressure to remove the ether. The residue was distilled in vacuo to give 2-(2-fluoro-4'-methoxy-4-biphenylyl)propionaldehyde, b.p. 153° – 156°C./0.2 mm.; m.p. 55° – 59°C. (novel intermediate D).

e. A solution of intermediate D (2.6 g.) in ethanol (8 ml.) was added to a stirred solution of sodium acetate (1.8 g.) and hydroxylamine sulphate (0.97 g.) in water (10 ml.). The mixture was stirred at room temperature for 2 hours, refluxed for 5 minutes and then cooled in ice. The resulting solid oxime was collected by filtration, washed with aqueous ethanol and dried in vacuo. A mixture of this oxime (2.6 g.), nickel sulphate (57 mg.) and water (16 ml.) was heated to boiling, after which aqueous sodium hydroxide (2.15 ml. 18N solution + 2 ml. water) was added and the mixture refluxed with stirring for 24 hours. The resulting solution was cooled to room temperature and acidified with dilute hydrochloric acid. The precipitated acid was extracted into ether and the resulting ethereal extract was extracted with aqueous potassium carbonate (2.5% w/$_v$ solution; 4 × 50 ml.). The combined aqueous extracts were acidified with dilute hydrochloric acid and the precipitated acid re-extracted into ether. The ethereal extract was washed with water, dried over anhydrous sodium sulphate and evaporated to dryness. The resulting solid residue was recrystallized from 1:1 benzene/light petroleum (b.p. 60° – 80°C.) to give 2-(2-fluoro-4'-methoxy-4-biphenylyl)propionic acid, m.p. 120° – 122°C. (novel intermediate E).

f. A mixture of intermediate E (0.306 g.), hydrobromic acid (9 ml. of 48% w/$_v$ acid), and glacial acetic acid (3 ml.) was refluxed for 3 hours, and then cooled. The solid product which separated on cooling was collected, washed with water and dried at 100°C. to give 2-(2-fluoro-4'-hydroxy-4-biphenylyl)propionic acid, m.p. 195° – 197°C.

EXAMPLE 2

4-fluoroiodobenzene and 4-bromo-3-nitroacetophenone were reacted in an analogous manner to that described in Example 1 (a) to give the novel intermediate 4-acetyl-4'-fluoro-2-nitrobiphenyl, m.p. 88° – 90°C. (from methanol). This compound was reduced with stannous chloride in concentrated hydrochloric acid in an analogous manner to that described in Example 1 (b) to give the novel intermediate 4-acetyl-2-amino-4'-fluorobiphenyl, m.p. 88° – 91°C. (from methanol). The amino group in this compound was converted to methoxy in the following way:

A solution of sodium nitrite (12.0 g.) in water (40 ml.) was added to a stirred solution of 4-acetyl-2-amino-4'-fluorobiphenyl (36.6 g.) in 5N sulphuric acid (480 ml.), whilst maintaining the temperature of the reaction mixture at 0° – 5°C. The reaction mixture was stirred at 0° – 5°C. for a further 1 hour. The resulting cold solution of diazonium salt was poured slowly into stirred refluxing 5N sulphuric acid (400 ml.). When the addition was complete, refluxing was continued for 0.5 hour. The resulting solution was poured into ice/water, causing the precipitation of a solid which was collected, dried and dissolved in ether. The ethereal solution was extracted with dilute aqueous sodium hydroxide and the extract was acidified to precipitate a product which was extracted into ether. The ethereal extract was washed with water, dried over anhydrous sodium sulphate, and evaporated to give a product which was recrystallized from light petroleum (b.p. 80° – 100°C.) to give the novel intermediate 4-acetyl-4'-fluoro-2-hydroxybiphenyl, m.p. 152° – 154°C. A mixture of this compound (36.5 g.), dimethyl sulphate (25.2 g.) and potassium carbonate (25 g.) in anhydrous acetone (200 ml.) was refluxed with stirring overnight. Acetone was removed by evaporation, the residue poured into water, and the resulting mixture extracted with ether. The ether extract was washed with dilute sodium hydroxide solution, then with water and dried over anhydrous sodium sulphate. Ether was removed by evaporation and the residue was distilled in vacuo to give a product, b.p. 142° – 144°C./0.2 mm. which solidified on cooling. This solid was recrystallized from light petroleum (b.p. 62° – 68°C.) to give the novel intermediate 4-acetyl-4'-fluoro-2-methoxybiphenyl, m.p. 75° – 77°C.

In an analogous manner to that described in Example 1 (d) and 1 (e), 4-acetyl-4'-fluoro-2-methoxybiphenyl was converted to the novel intermediate 2-(4'-fluoro-2-methoxy-4-biphenylyl)propionaldehyde, b.p. 144° – 146°C./0.3 mm., and thence to the novel intermediate 2-(4'-fluoro-2-methoxy-4-biphenylyl)propionic acid, m.p. 133° – 136°C. (from light petroleum, b.p. 100° – 120°C.).

A solution of 2-(4'-fluoro-2-methoxy-4-biphenylyl)-propionic acid (10 g.) in a mixture of hydrobromic acid (270 ml. of 48%w/$_v$ aqueous acid) and glacial acetic acid (90 ml.) was refluxed for 3.5 hours. The resulting solution was poured onto crushed ice, causing the precipitation of a solid product. This product was collected by filtration, washed with water, dried and recrystallised from chloroform/light petroleum (b.p. 62° – 68°C.) to give 2-(4'-fluoro-2-hydroxy-4-biphenylyl)-propionic acid, m.p. 138° – 142°C.

EXAMPLE 3

4-acetyl-2-amino-4'-methoxybiphenyl was converted to the novel intermediate 4-acetyl-2-hydroxy-4'-methoxybiphenyl, m.p. 161°– 162°C. (from ethanol) and thence to the novel intermediate 4-acetyl-2,4'-dimethoxybiphenyl, m.p. 77° – 79°C. (from ethanol) by diazotization and methylation methods analogous to those described in Example 2.

By methods analogous to those described in Example 1 (d) and 1 (e), 4-acetyl-2,4'-dimethoxybiphenyl was converted to the novel intermediate 2-(2,4'-dimethoxy-4-biphenylyl) propionaldehyde and thence to the novel intermediate 2-(2,4'-dimethoxy-4-biphenylyl)-propionic acid, m.p. 113° – 115°C. (from 1:1 benzene/light petroleum, b.p. 62° – 68°C.

This was then converted to 2-(2,4'-dihydroxy-4-biphenylyl)propionic acid, m.p. 190° – 192°C. from benzene/light petroleum (b.p. 62° – 68°C.) by reaction with hydrobromic acid in acetic acid in an analogous manner to that described in Example 1 (f).

EXAMPLE 4

By methods analogous to those described in Example 1 (d) and 1 (e), 4-acetyl-4'-methoxybiphenyl was converted to the novel intermediate 2-(4'-methoxy-4- biphenylyl) propionaldehyde and thence to the novel intermediate 2-(4'-methoxy-4-biphenylyl)propionic acid, m.p. 181° – 184°C. (from benzene).

This was converted to 2-(4'-hydroxy-4-biphenylyl)-propionic acid, m.p. 204° – 207°C. (from ethyl acetate/light petroleum, b.p. 60° – 80°C.), by reaction with hydrobromic acid in acetic acid in an analogous manner to that described in Example 1 (f).

EXAMPLE 5

4-chloroiodobenzene and 4-bromo-3-nitroacetophenone were reacted in an analogous manner to that described in Example 1 (a) to give the novel intermediate 4-acetyl-4'-chloro-2-nitrobiphenyl, m.p. 103° – 105°C. (from methanol). This compound was reduced with stannous chloride and concentrated hydrochloric acid in an analogous manner to that described in Example 1 (b) to give the novel intermediate 4-acetyl-2-amino-4'-chlorobiphenyl, m.p. 139° – 140°C. (from methanol). This compound was converted to the novel intermediate 4-acetyl-4'-chloro-2-hydroxybiphenyl and thence to the novel intermediate 4-acetyl-4'-chloro-2-methoxybiphenyl, b.p. 167° – 170°C./0.4 mm., by diazotization and methylation methods analogous to those described in Example 2.

By methods analogous to those described in Example 1 (d) and 1 (e), 4-acetyl-4'-chloro-2-methoxybiphenyl was converted to the novel intermediate 2-(4'-chloro-2-methoxy-4-biphenylyl)propionaldehyde, b.p. 174° – 175°C./0.7 mm. (solidified on cooling) and thence to the novel intermediate 2-(4'-chloro-2-methoxy-4-biphenylyl)propionic acid, m.p. 127° – 128°C. (from light petroleum, b.p. 80° – 100°C.)

This was converted to 2-(4'-chloro-2-hydroxy-4-biphenylyl)propionic acid, m.p. 134° – 135°C. (from light petroleum, b.p. 80° – 100°C.) by reaction with hydrobromic acid in acetic acid in an analogous manner to that described in Example 1 (f).

EXAMPLE 6

To a stirred mixture of sodium (0.97 g.) in absolute ethanol (30 ml.) was added diethyl methylmalonate (9.2 ml.) followed by the addition of a solution of 2-phenyl-o-quinol acetate (9.8 g.) in warm absolute ethanol (120 ml.). The mixture was refluxed with stirring for 3.5 hours, and then ethanol was removed by evaporation under reduced pressure. To the residue was added 2.5N aqueous sodium hydroxide (78 ml.) and the mixture refluxed for 1.5 hours. The resulting solution was cooled and acidified to precipitate a product which was collected by filtration, washed with water and dried in vacuo to give the novel intermediate 2-(2-hydroxy-4-biphenylyl)-2-methylmalonic acid. This compound was heated at 200°C. for 20 minutes to give a product which was recrystallized from benzene and then light petroleum, b.p. 80° – 100°C., to give 2-(2-hydroxy-4-biphenylyl)propionic acid, m.p. 120° – 124°C.

EXAMPLE 7

By methods analogous to those described in Example 2, 4-acetyl-2-amino-2',4'-difluorobiphenyl was converted to the novel intermediate 4-acetyl-2',4'-difluoro-2-hydroxybiphenyl, m.p. 171° – 173°C. (from industrial methylated spirits), and thence to the novel intermediate, 4-acetyl-2',4'-difluoro-2-methoxybiphenyl, m.p. 89° – 91°C. (from light petroleum b.p. 62° – 68°C.).

By methods analgous to those described in Example 1 (d) and 1 (e) this was then converted to crude 2-(2',4'-difluoro-2-methoxy-4-biphenylyl)propionaldehyde and thence to the novel intermediate 2-(2',4'-difluoro-2-methoxy-4-biphenylyl)propionic acid, m.p. 148° – 149°C. (from methylene chloride/light petroleum b.p. 62° – 68°C.).

This was then converted to 2-(2',4'-difluoro-2-hydroxy-4biphenylyl)propionic acid, m.p. 138° – 140°C. (from chloroform) by reaction with hydrobromic acid in acetic acid in an analogous manner to that described in Example 1 (f).

EXAMPLE 8

4-Acetyl-2-amino-2'-methoxybiphenyl was diazotized and the diazonium solution poured onto an ice cold aqueous solution of hyprophosphorous acid which was stirred at 0°C. for 4 hours and left at room temperature overnight. The precipitate product was collected, washed with water and dried in vacuo. The product was dissolved in a 1:1 mixture of chloroform and ethanol and the chloroform removed azeotropically. The crystals were separated off and washed with ethanol and dried in vacuo to give the novel intermediate, 4-acetyl-2'-methoxybiphenyl, m.p. 98° – 100°C. This was then converted, by methods analogous to those described in Example 1 (d) and 1 (e) to crude 2-(2-methoxy-4-biphenylyl)propionaldehyde and then to the novel intermediate 2-(2-methoxy-4-biphenyl)propionic acid, m.p. 146° – 148°C. (from benzene).

This was then converted to 2-(2'-hydroxy-4-biphenylyl) propionic acid, m.p. 97° – 98°C. (from 1:10 benzene/light petroleum, b.p. 80° – 100°C.) by reaction with hydrobromic acid in acetic acid in an analogous manner to that described in Example 1 (f).

EXAMPLE 9

2-(2-fluoro-4-biphenylyl)propionic acid (1 g.) ethylene glycol (10 ml.) and potassium hydroxide (0.8 g.) were refluxed under nitrogen for 24 hours. The mixture was diluted with water, washed with ether, acidified with hydrochloric acid and extracted with ether. The ether extract was washed with water, dried and evaporated to dryness. The product was subjected to thin layer chromatography to give 2-(2-hydroxy-4-biphenylyl)propionic acid, which was recrystallized from light petroleum (b.p. 80° – 100°C.) to give the purified acid having a m.p. of 112° – 119°C.

EXAMPLE 10

In a similar manner to Example 9 there was obtained from 2-(2'-fluoro-4-biphenylyl)propionic acid, 2-(2'-hydroxy-4-biphenylyl)propionic acid, m.p. 97.5° – 98.5°C.

EXAMPLE 11

An ethereal solution of 2-(2-hydroxy-4-biphenylyl) propionic acid was treated with excess diazomethane and the resulting mixture evaporated to dryness under reduced pressure. The resulting product was triturated with light petroleum, b.p. 40° – 60°C., collected by filtration and dried. The product was recrystallised twice from light petroleum (b.p. 80° – 100°C.) to give methyl 2-(2-hydroxy-4-biphenylyl)propionate, m.p. 105.5° – 107.5°C.

EXAMPLE 12

A solution of 2-(2',4'-difluoro-2-hydroxy-4-diphenylyl) propionic acid (4.5 g.) in absolute ethanol (50 ml.) containing concentrated sulphuric acid (2 ml.) was refluxed overnight (16 hours). After distillation of ethanol the residue was poured onto ice-water and the product was isolated in ether. The extracts were washed with dilute sodium bicarbonate dried and evaporated. The solid residue thus obtained was purified by two crystallizations from light petrol (b.p. 62° – 68°C.), to give ethyl 2-(2',4'-difluoro-2-hydroxy-4-biphenylyl)propionate, m.p. 72° – 73°C.

EXAMPLE 13

A solution of ethyl 2-(2',4'-difluoro-2-hydroxy-4-biphenylyl)propionate (2.0 g.), from the previous Example, in dry ether (40 ml.) was added over 15 minutes in dry ether (40 ml.). After stirring under reflux for 1.5 hours, excess lithium aluminium hydride was decomposed by the cautious addition of water and finally with 2N sulphuric acid (10 ml.). The product was isolated in ether, washed, dried, evaporated and distilled to give a thick translucent oil, setting to a hard glass on cooling. Trituration with boiling light petroleum (b.p. 62° – 68°C.) gave a crystalline solid. This was recrystallized from methylene chloride/light petroleum (b.p. 40° – 60°C.) to give 2-(2'4'-difluoro-2-hydroxy-4-diphenylyl)propan-l-ol, m.p. 118° –118.5°C.

EXAMPLE 14

A solution of 2-(2',4'-difluoro-2-hydroxy-4-biphenylyl) propionic acid (1.75 g.) and thionyl chloride (1 ml.) in dry benzene (10 ml.) was refluxed for 1 hour and then cooled and added dropwise to stirred cold ammonia (d=0.880 g./ml; 20 ml.). The product was filtered and recrystallised first from aqueous industrial methylated spirits and then light petroleum (b.p. 62° – 68°C.) to give 2-(2',4'difluoro-2-hydroxy-4-biphenylyl)propionamide, m.p. 222° – 224°C.

EXAMPLE 15

A solution of 2-(2',4'-difluoro-2-hydroxy-4-diphenylyl) propionic acid (1 g.) and 2-amino-2-methylpropan-1-ol (1 ml.) in xylene (20 ml.) was stirred under reflux for 3 days. The solvent was distilled and the solid residue was recrystallised from aqueous methanol to give 2-[1-(2',4'-difluoro-2-hydroxy-4-biphenylyl)ethyl]-4,4-dimethyl-2-oxazoline, m.p. 188° – 194°C. (decomposes).

EXAMPLE 16

By methods analogous to those described in Example 2, 4-acetyl-2'-amino-2'-chloro-4'-fluoro biphenyl was converted to the novel intermediate 4-acetyl-2'-chloro-4'-fluoro-2-methoxybiphenyl, m.p. 81.5° – 83.5°C. By methods analogous to those described in Example 1 (d) and 1 (e) this was converted to crude 2-(2'-chloro-4'-fluoro-2methoxy-4-biphenylyl) propionaldehyde and thence to the novel intermediate 2-(2'-chloro-4'-fluoro-2-methoxy-4-biphenylyl)propionic acid, m.p. 138° – 140°C.

This was then converted to 2-(2'-chloro-4'-fluoro-2-hydroxy-4-biphenylyl)propionic acid, m.p. 155° – 157.5°C., by reaction with hydrobromic acid, in acetic acid in an analogous manner to that described in Example 1 (f).

EXAMPLE 17

By methods analogous to 2'described in Example 1 (a) and (b), 4-iodo-3-methoxy anisole and 4'-bromo-3'-nitroacetophenone were reacted to give the novel intermediate 4-acetyl-2',4'-dimethoxy-2-nitrobiphenyl, m.p. 129° – 131°C. which was converted to the novel intermediate 4acetyl-2-amino-2;40 ,4'-dimethoxybiphenyl, m.p. 149° – 151°C. This (15.7 g.) was diazotized and the diazonium solution added slowly to a solution of cuprous chloride (7.5 g.) in 4N hydrochloric acid (70 ml.) at 0°C. The mixture was warmed to room temperature over 1 hour and then heated for a further hour on a steam bath. The solution was cooled and made alkaline (pH14) with 18N caustic soda. The product was extracted with methylene chloride, the extract dried and the solvent evaporated off to give a brown oil which was extracted with ether. The ether was evaporated and the residual oil distilled and the distillate recrystallised from isopropanol to give the novel intermediate 4-acetyl-2-chloro-2',4'-dimethoxybiphenyl m.p. 115° – 118°C. By methods analogous to those described in Example 1 (d) and 1 (e) this was converted to crude 2-(2-chloro-2',4'-dimethoxy-4-biphenylyl)propionaldehyde and thence to the novel intermediate 2-(2-chloro-2',4'-dimethoxy-4-biphenylyl) propionic acid, obtained as an oil.

This was then converted to 2-(2-chloro-2',4'-dihydroxy-4-biphenylyl)propionic acid, obtained as a glass by reaction with hydrobromic acid in acetic acid, in an analogous manner to that described in Example 1 (f).

EXAMPLE 18

By methods analogous to those described in Example 1 (a) and (b), 4-chloro-2-iodo anisole and 4'-bromo-3'-nitroacetophenone were reacted to give the novel intermediate 4-acetyl-4'-chloro-2'-methoxy-2-nitrobiphenyl, m.p. 108° – 109°C. which was converted to the novel intermediate 4-acetyl-2-amino-4'-chloro-2'-methoxybiphenyl, m.p. 104° – 106°C.

By methods analogous to those described in Example 17 this was converted to the novel intermediate 4-acetyl-2,4'-dichloro-2'-methoxybiphenyl, m.p. 80° – 82°C.

By methods analogous to those described in Example 1 (d) and (c) this was converted to crude 2-(2,4'-dichloro-2'-methoxy-4-biphenylyl)propionaldehyde and thence to the novel intermediate, 2-(2-4'-dichloro-2'-methoxy-4biphenylyl) propionic acid, obtained as an oil.

This was then converted to 2-(2,4'-dichloro-2'-hydroxy-4-biphenylyl)propionic acid, obtained as a glass by reaction with hydrobromic acid in acetic acid in an analogous manner to that described in Example 1 (f).

EXAMPLE 19

2-(2-hydroxy-4-biphenylyl)propionic acid was mixed with an equivalent amount of aqueous sodium hydroxide. The mixture was evaporated to dryness to give sodium 2-(2-hydroxy-4-biphenylyl)propionate, m.p. 230 (decomposed) °C.

EXAMPLE 20

2-(2-hydroxy-4-biphenylyl)propionic acid (140 mg.) in ether (5 ml.) was mixed with benzylamine (62 g.) in ether (5 ml.). The precipitate was collected, washed with ether, dried in vacuo and recrystallised for absolute alcohol/ether to give benzylammonium 2-(2-hydroxy4-biphenylyl) propionate, m.p. 183° – 185°C.

EXAMPLE 21

Hard gelatin capsules were prepared each containing the following ingredients.

| | | |
|---|---|---|
| (a) | 2-(2-fluoro-4'-hydroxy-4-biphenylyl)propionic acid | 5 mg. |
| | lactose | 95 mg. |
| (b) | 2-(2-fluoro-4'-hydroxy-4-biphenyl)prioionic acid | 10 mg. |
| | calcium phosphate | 5 mg. |
| | maize starch | 85 mg. |
| (c) | 2-(2-fluoro-4'-hydroxy-4-biphenylyl)propionic acid | 10 mg. |
| | maize starch | 30 mg. |
| | lactose | 30 mg. |
| | calcium phosphate | 30 mg. |

Similar capsules are prepared containing as the active ingredient the substituted hydroxy propionic acids and their derivatives of Examples 2 to 20.

EXAMPLE 22

The following mixture was formed into tablets in a conventional manner, each tablet containing 10 mg. of active ingredient.

| | parts |
|---|---|
| 2-(2-hydroxy-4-biphenylyl)propionic acid | 10 |
| maize starch | 30 |
| lactose | 158 |
| stearic acid | 1 |
| magnesium stearate | 1 |

Similar tablets are prepared containing as the active ingredient the substituted hydroxy propionic acids and their derivatives of Examples 1–5, 7, 8 and 10 to 20.

EXAMPLE 23

4-Acetyl-2-amino-4'-chloro-2'-methoxybiphenyl from Example 18, was deaminated in an analogous manner to that described in Example 8 to give 4-acetyl-4'-chloro-2'methoxybiphenyl. By methods analogous to those described in Example 1 (d), (e) and (f) this was converted to crude 2-(4'-chloro-2'-methoxy-4-biphenylyl)jjpropionaldehyde and thence to the crude acid which was then converted to 2-(4'-chloro-2'-hydroxy-4-biphenylyl)propionic acid, m.p. 125° – 127°C.

We claim:

1. 2-(2-Hydroxy-4-biphenylylpropionic acid.

* * * * *